United States Patent
Chinta et al.

(10) Patent No.: US 8,785,705 B2
(45) Date of Patent: Jul. 22, 2014

(54) USE OF A CO-FEED IN THE COUPLING OF TOLUENE WITH A CARBON SOURCE

(75) Inventors: Sivadinarayana Chinta, Missouri City, TX (US); Joseph L. Thorman, Milwaukee, WI (US); James R. Butler, Spicewood, TX (US)

(73) Assignee: Fina Technology, Inc., Houston, TX (US)

(*) Notice: Subject to any disclaimer, the term of this patent is extended or adjusted under 35 U.S.C. 154(b) by 168 days.

(21) Appl. No.: 13/457,500

(22) Filed: Apr. 27, 2012

(65) Prior Publication Data

US 2012/0296137 A1    Nov. 22, 2012

Related U.S. Application Data

(60) Provisional application No. 61/488,772, filed on May 22, 2011.

(51) Int. Cl.
*C07C 15/46* (2006.01)
*C07C 15/073* (2006.01)

(52) U.S. Cl.
USPC ............................. 585/437; 585/469

(58) Field of Classification Search
CPC ........ C07C 2/867; C07C 2/865; C07C 2/864; C07C 15/073; C07C 15/46; C07C 2529/06
USPC .................................... 585/467, 469
See application file for complete search history.

(56) References Cited

U.S. PATENT DOCUMENTS

| | | | |
|---|---|---|---|
| 4,463,204 A * | 7/1984 | Liu | ............................... 585/437 |
| 4,499,318 A | 2/1985 | Liu | |
| 4,806,699 A | 2/1989 | Smith et al. | |
| 5,026,937 A | 6/1991 | Bricker | |
| 5,849,969 A | 12/1998 | Heyse et al. | |
| 2008/0293980 A1 | 11/2008 | Kiesslich et al. | |

* cited by examiner

*Primary Examiner* — Thuan D Dang

(57) ABSTRACT

A process for making styrene is disclosed that includes providing toluene, a co-feed, and a $C_1$ source to a reactor containing a catalyst, reacting toluene with the $C_1$ source in the presence of the catalyst and the co-feed to form a product stream containing ethylbenzene and styrene. The co-feed can be selected from the group of water, carbon monoxide, hydrogen, and combinations thereof.

12 Claims, 2 Drawing Sheets

USE OF A CO-FEED IN THE COUPLING OF TOLUENE WITH A CARBON SOURCE

CROSS-REFERENCE TO RELATED APPLICATIONS

This application claims priority to U.S. Provisional Patent No. 61/488,772 filed on May 22, 2011.

FIELD

The present invention relates to a method for the production of styrene and ethylbenzene. More specifically, the invention relates to the alkylation of toluene with a carbon source (herein referred to as a $C_1$ source) such as methanol and/or formaldehyde, to produce styrene and ethylbenzene.

BACKGROUND

Styrene is a monomer used in the manufacture of many plastics. Styrene is commonly produced by making ethylbenzene, which is then dehydrogenated to produce styrene. Ethylbenzene is typically formed by one or more aromatic conversion processes involving the alkylation of benzene.

Aromatic conversion processes, which are typically carried out utilizing a molecular sieve type catalyst, are well known in the chemical processing industry. Such aromatic conversion processes include the alkylation of aromatic compounds such as benzene with ethylene to produce alkyl aromatics such as ethylbenzene. Typically an alkylation reactor, which can produce a mixture of monoalkyl and polyalkyl benzenes, will be coupled with a transalkylation reactor for the conversion of polyalkyl benzenes to monoalkyl benzenes. The transalkylation process is operated under conditions to cause disproportionation of the polyalkylated aromatic fraction, which can produce a product having an enhanced ethylbenzene content and reduced polyalkylated content. When both alkylation and transalkylation processes are used, two separate reactors, each with its own catalyst, can be employed for each of the processes.

Ethylene is obtained predominantly from the thermal cracking of hydrocarbons, such as ethane, propane, butane, or naphtha. Ethylene can also be produced and recovered from various refinery processes. Thermal cracking and separation technologies for the production of relatively pure ethylene can account for a significant portion of the total ethylbenzene production costs.

Benzene can be obtained from the hydrodealkylation of toluene that involves heating a mixture of toluene with excess hydrogen to elevated temperatures (for example 500° C. to 600° C.) in the presence of a catalyst. Under these conditions, toluene can undergo dealkylation according to the chemical equation: $C_6H_5CH_3 + H_2 \rightarrow C_6H_6 + CH_4$. This reaction requires energy input and as can be seen from the above equation, produces methane as a byproduct, which is typically separated and may be used as heating fuel for the process.

Another known process includes the alkylation of toluene to produce styrene and ethylbenzene. In this alkylation process, various aluminosilicate catalysts are utilized to react methanol and toluene to produce styrene and ethylbenzene. However, such processes have been characterized by having very low yields in addition to having very low selectivity to styrene and ethylbenzene.

Also, the aluminosilicate catalysts are typically prepared using solutions of acetone and other highly flammable organic substances, which can be hazardous and require additional drying steps. For instance a typical aluminosilicate catalyst can include various promoters supported on a zeolitic substrate. These catalysts can be prepared by subjecting the zeolite to an ion-exchange in an aqueous solution followed by a promoter metal impregnation using acetone. This method requires an intermediate drying step after the ion-exchange to remove all water prior to the promoter metal impregnation with acetone. After the promoter metal impregnation the catalyst is subjected to a further drying step to remove all acetone. This intermediate drying step typically involves heating to at least 150° C., which results in increased costs.

In view of the above, it would be desirable to have a process of producing styrene and/or ethylbenzene that does not rely on thermal crackers and expensive separation technologies as a source of ethylene. It would further be desirable to avoid the process of converting toluene to benzene with its inherent expense and loss of a carbon atom to form methane. It would be desirable to produce styrene without the use of benzene and ethylene as feedstreams. It would also be desirable to produce styrene and/or ethylbenzene in one reactor without the need for separate reactors requiring additional separation steps. Furthermore, it is desirable to achieve a process having a high yield and selectivity to styrene and ethylbenzene. Even further, it is desirable to achieve a process having a high yield and selectivity to styrene such that the step of dehydrogenation of ethylbenzene to produce styrene can be reduced. It is further desirable to be able to produce a catalyst having the properties desired without involving flammable materials and/or intermediate drying steps.

SUMMARY

The present invention in its many embodiments relates to a process of making styrene. In an embodiment of the present invention, a process is provided for making styrene including providing toluene, a co-feed, and a $C_1$ source to a reactor including a catalyst and reacting toluene with the $C_1$ source in the presence of the catalyst and the co-feed to form a product stream including ethylbenzene and styrene. The co-feed is selected from the group of water, carbon monoxide, hydrogen, and combinations thereof.

In an embodiment, either by itself or in combination with any other embodiment, the $C_1$ source can be selected from the group of methanol, formaldehyde, formalin, trioxane, methylformcel, paraformaldehyde, methylal, dimethyl ether, and combinations thereof.

In an embodiment, either by itself or in combination with any other embodiment, the catalyst includes at least one promoter on a support material. The promoter can be selected from the group of Co, Mn, Ti, Zr, V, Nb, K, Cs, Ga, B, P, Rb, Ag, Na, Cu, Mg, Fe, Mo, Ce, and combinations thereof. Optionally, the promoter is selected from the group of Ce, Cu, P, Cs, B, Co, Ga, and combinations thereof. The support material can include a zeolite. The catalyst can include B and Cs supported on a zeolite.

In an embodiment, either by itself or in combination with any other embodiment, the co-feed is present in amounts of 0.0001 to 15 wt % of the combined feed of the toluene, co-feed and $C_1$ source.

In an embodiment, either by itself or in combination with any other embodiment, the toluene conversion ranges from 2 to 50%.

In an embodiment, either by itself or in combination with any other embodiment, the selectivity to styrene ranges from 15 to 80%.

In an embodiment, either by itself or in combination with any other embodiment, the selectivity to ethylbenzene ranges from 15 to 80%.

Another embodiment of the present invention includes a method of making styrene including providing a reactor including a catalyst; contacting the catalyst with a co-feed and a reactant feed stream including toluene and a $C_1$ source; and reacting the toluene with the $C_1$ source in the presence of the catalyst to form a product stream including ethylbenzene and styrene. The $C_1$ source can be selected from the group of methanol, formaldehyde, formalin, trioxane, methylformcel, paraformaldehyde, methylal, dimethyl ether, and combinations thereof.

The various embodiments of the present invention can be joined in combination with other embodiments of the invention and the listed embodiments herein are not meant to limit the invention. All combinations of embodiments of the invention are enabled, even if not given in a particular example herein.

DETAILED DESCRIPTION

Figure 1:
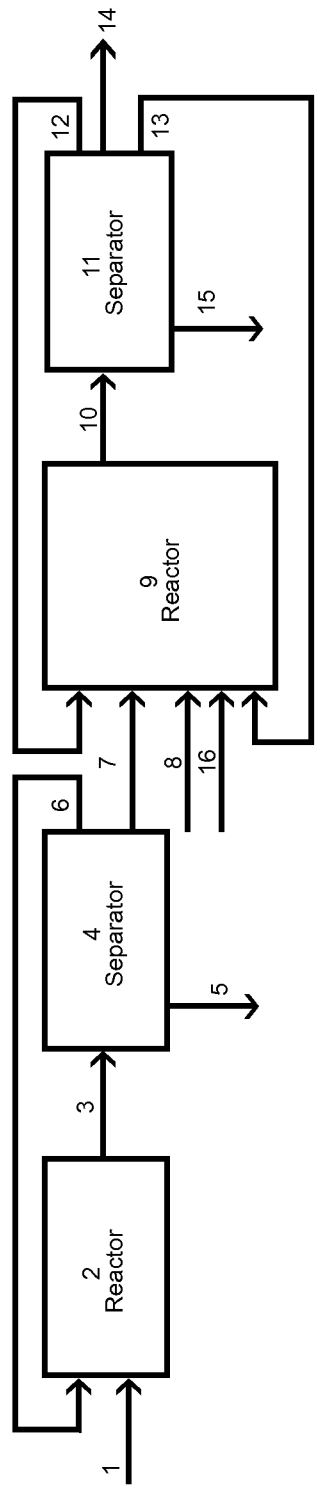
FIG. 1 illustrates a flow chart for the production of styrene by the reaction of formaldehyde and toluene, wherein the formaldehyde is first produced in a separate reactor by either the dehydrogenation or oxidation of methanol and is then reacted with toluene to produce styrene.

In accordance with an embodiment of the current invention, toluene is reacted with a carbon source capable of coupling with toluene to form ethylbenzene or styrene, which can be referred to as a $C_1$ source, in the presence of a co-feed to produce styrene and ethylbenzene. In an embodiment, the $C_1$ source includes methanol or formaldehyde or a mixture of the two. In an embodiment, the co-feed includes one or more of carbon monoxide (CO), water ($H_2O$), or hydrogen ($H_2$). In an alternative embodiment, toluene is reacted with one or more of the following: formalin (37-50% $H_2CO$ in solution of water and MeOH), trioxane (1,3,5-trioxane), methylformcel (55% $H_2CO$ in methanol), paraformaldehyde, methylal (dimethoxymethane), and dimethyl ether. In a further embodiment, the $C_1$ source is selected from the group of methanol, formaldehyde, formalin, trioxane, methylformcel, paraformaldehyde, methylal, dimethyl ether, and combinations thereof.

Formaldehyde can be produced either by the oxidation or dehydrogenation of methanol.

In an embodiment, formaldehyde is produced by the dehydrogenation of methanol to produce formaldehyde and hydrogen gas. This reaction step produces a dry formaldehyde stream that may be preferred, as it would not require the separation of the water prior to the reaction of the formaldehyde with toluene. The dehydrogenation process is described in the equation below:

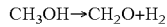
$$CH_3OH \rightarrow CH_2O + H_2$$

Formaldehyde can also be produced by the oxidation of methanol to produce formaldehyde and water. The oxidation of methanol is described in the equation below:

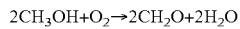
$$2CH_3OH + O_2 \rightarrow 2CH_2O + 2H_2O$$

In the case of using a separate process to obtain formaldehyde, a separation unit may then be used in order to separate the formaldehyde from the hydrogen gas or water from the formaldehyde and unreacted methanol prior to reacting the formaldehyde with toluene for the production of styrene. This separation would inhibit the hydrogenation of the formaldehyde back to methanol. Purified formaldehyde could then be sent to a styrene reactor and the unreacted methanol could be recycled.

In accordance with the present invention, CO and/or $H_2$ may be added in the presence of the coupling reaction in order to restrict the destruction of formaldehyde. The effect of the presence of added CO and/or $H_2$ on preserving formaldehyde is demonstrated in the following equations below:

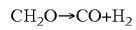
$$CH_2O \rightarrow CO + H_2$$

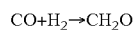
$$CO + H_2 \rightarrow CH_2O$$

Although the coupling reaction has a 1:1 molar ratio of toluene and the $C_1$ source, the ratio of the $C_1$ source and toluene feedstreams is not limited within the present invention and can vary depending on operating conditions and the efficiency of the reaction system. If excess toluene or $C_1$ source is fed to the reaction zone, the unreacted portion can be subsequently separated and recycled back into the process. In one embodiment the ratio of toluene:$C_1$ source can range from between 100:1 to 1:100. In alternate embodiments the ratio of toluene:$C_1$ source can range from 50:1 to 1:50; from 20:1 to 1:20; from 10:1 to 1:10; from 5:1 to 1:5; from 2:1 to 1:2. In a specific embodiment, the ratio of toluene:$C_1$ source can range from 3:1 to 1:1.

In an embodiment, the reactants, toluene and the $C_1$ source are combined with a co-feed. In an embodiment, the co-feed is selected from the group of hydrogen, carbon monoxide, and water, and any combinations thereof. In another embodiment, the co-feed may be combined with nitrogen prior to combining the co-feed with the reactants. The co-feed may be combined with the reactants in any desired amounts. In an embodiment, the co-feed is added in amounts ranging from 0.0001 wt % to 15 wt % of the total feed, optionally from 0.01 wt % to 10 wt % of the total feed, optionally from 0.1 wt % to 5 wt % of the total feed, optionally from 0.1 wt % to 2.5 wt % of the total feed.

In FIG. 1 there is a simplified flow chart of one embodiment of the styrene production process described above. In this embodiment, a first reactor (2) is either a dehydrogenation reactor or an oxidation reactor. This reactor is designed to convert the first methanol feed (1) into formaldehyde. The gas product (3) of the reactor is then sent to a gas separation unit (4) where the formaldehyde is separated from any unreacted methanol and unwanted byproducts. Any unreacted methanol (6) can then be recycled back into the first reactor (2). The byproducts (5) are separated from the clean formaldehyde (7).

In one embodiment the first reactor (2) is a dehydrogenation reactor that produces formaldehyde and hydrogen and the separation unit (4) is a membrane capable of removing hydrogen from the product stream (3).

In an alternate embodiment the first reactor (2) is an oxidative reactor that produces product stream (3) comprising formaldehyde and water. The product stream (3) comprising formaldehyde and water can then be sent to the second reactor (9) without a separation unit (4).

The formaldehyde feed stream (7) is then reacted with a feed stream of toluene (8) and a co-feed stream (16) in a second reactor (9). The toluene and formaldehyde react to produce styrene. The product (10) of the second reactor (9) may then be sent to an optional separation unit (11) where any unwanted byproducts (15) such as water can separated from the styrene, unreacted formaldehyde and unreacted toluene. Any unreacted formaldehyde (12) and the unreacted toluene (13) can be recycled back into the reactor (9). A styrene product stream (14) can be removed from the separation unit (11) and subjected to further treatment or processing if desired.

The operating conditions of the reactors and separators will be system specific and can vary depending on the feedstream composition and the composition of the product streams. The reactor (9) for the reaction of toluene and formaldehyde will operate at elevated temperatures and may contain a basic or neutral catalyst system. The temperature can range in a non-limiting example from 250° C. to 750° C., optionally from 300° C. to 500° C., optionally from 375° C. to 450° C. The pressure can range in a non-limiting example from 0.1 atm to 70 atm, optionally from 0.1 atm to 35 atm, optionally from 0.1 atm to 10 atm, optionally from 0.1 atm to 5 atm.

Figure 2:
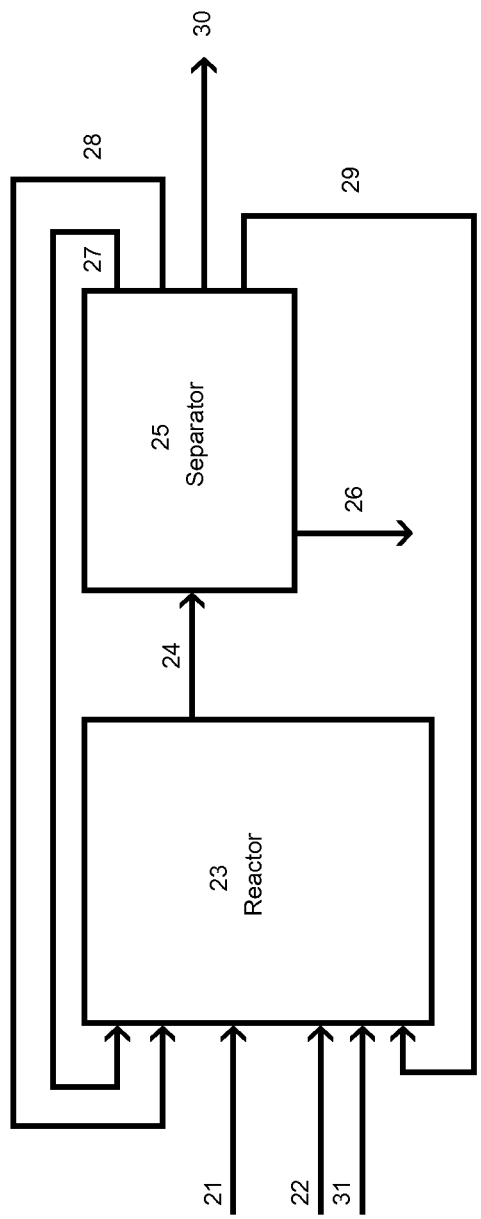
FIG. 2 illustrates a flow chart for the production of styrene by the reaction of formaldehyde and toluene, wherein methanol and toluene are fed into a reactor, wherein the methanol is converted to formaldehyde and the formaldehyde is reacted with toluene to produce styrene.

FIG. 2 is a simplified flow chart of another embodiment of the styrene process discussed above. A $C_1$ source containing feed stream (21) is fed along with a feed stream of toluene (22) and a co-feed stream (31) in a reactor (23). Toluene and the $C_1$ source then react to produce styrene. The product (24) of the reactor (23) may then be sent to an optional separation unit (25) where any unwanted byproducts (26) can be separated from the styrene, and any unreacted $C_1$ source, unreacted methanol, unreacted formaldehyde and unreacted toluene. Any unreacted methanol (27), unreacted formaldehyde (28) and the unreacted toluene (29) can be recycled back into the reactor (23). A product stream (30) that can include styrene and ethylbenzene can be removed from the separation unit (25) and subjected to further treatment or processing if desired.

The operating conditions of the reactors and separators will be system specific and can vary depending on the feedstream composition and the composition of the product streams. The reactor (23) for the reactions of methanol to formaldehyde and toluene with a $C_1$ source, such as formaldehyde, will operate at elevated temperatures and pressures and may contain a basic or neutral catalyst system. The temperature can range in a non-limiting example from 250° C. to 750° C., optionally from 350° C. to 550° C., optionally from 375° C. to 475° C. The pressure can range in a non-limiting example from 0.1 atm to 70 atm, optionally from 0.1 atm to 10 atm, optionally from 0.1 atm to 3 atm.

Improvement in side chain alkylation selectivity may be achieved by treating a molecular sieve zeolite catalyst with chemical compounds to inhibit the external acidic sites and minimize aromatic alkylation on the ring positions. Another means of improvement of side chain alkylation selectivity can be to inhibit overly basic sites, such as for example with the addition of a boron compound. Another means of improvement of side chain alkylation selectivity can be to impose restrictions on the catalyst structure to facilitate side chain alkylation. In one embodiment the catalyst used in an embodiment of the present invention is a basic or neutral catalyst.

The catalytic reaction systems suitable for this invention can include one or more of the zeolite or amorphous materials modified for side chain alkylation selectivity. A non-limiting example can be a zeolite promoted with one or more of the following: Co, Mn, Ti, Zr, V, Nb, K, Cs, Ga, B, P, Rb, Ag, Na, Cu, Mg, Fe, Mo, Ce, or combinations thereof. In an embodiment, the zeolite can be promoted with one or more of Ce, Cu, P, Cs, B, Co, Ga, or combinations thereof. The promoter can exchange with an element within the zeolite or amorphous material and/or be attached to the zeolite or amorphous material in an occluded manner. In an embodiment the amount of promoter is determined by the amount needed to yield less than 0.5 mol % of ring alkylated products such as xylenes from a coupling reaction of toluene and a $C_1$ source.

In an embodiment, the catalyst contains greater than 0.1 wt % of at least one promoter based on the total weight of the catalyst. In another embodiment, the catalyst contains up to 5 wt % of at least one promoter. In a further embodiment, the catalyst contains from 0.1 to 3 wt % of at least one promoter, optionally from 0.1 to 1 wt % of at least one promoter. In an embodiment, the at least one promoter is boron.

Zeolite materials suitable for this invention may include silicate-based zeolites and amorphous compounds such as faujasites, mordenites, etc. Silicate-based zeolites are made of alternating $SiO_4^-$ and $MO_x$ tetrahedra, where M is an element selected from the Groups 1 through 16 of the Periodic Table (new IUPAC). These types of zeolites have 4, 6, 8, 10, or 12-membered oxygen ring channels. An example of zeolites of this invention can include faujasites, such as an X-type or Y-type zeolite and zeolite beta. Zeolite-like materials can also be an effective substrate. Alternate molecular sieves also contemplated are zeolite-like materials such as the crystalline silicoaluminophosphates (SAPO) and the aluminophosphates (ALPO) and the like.

In an embodiment, the zeolite materials suitable for this invention are characterized by silica to alumina ratio (Si/Al) of less than 1.5. In another embodiment, the zeolite materials are characterized by a Si/Al ratio ranging from 1.0 to 200, optionally from 1.0 to 100, optionally from 1.0 to 50, optionally from 1.0 to 10, optionally from 1.0 to 2.0, optionally from 1.0 to 1.5.

The present catalyst is adaptable to use in the various physical forms in which catalysts are commonly used. The catalyst of the invention may be used as a particulate material in a contact bed or as a coating material on structures having a high surface area. If desired, the catalyst can be deposited with various catalyst binder and/or support materials.

A catalyst comprising a substrate that supports a promoting metal or a combination of metals can be used to catalyze the reaction of hydrocarbons. The method of preparing the catalyst, pretreatment of the catalyst, and reaction conditions can influence the conversion, selectivity, and yield of the reactions.

The various elements that make up the catalyst can be derived from any suitable source, such as in their elemental form, or in compounds or coordination complexes of an organic or inorganic nature, such as carbonates, oxides, hydroxides, nitrates, acetates, chlorides, phosphates, sulfides and sulfonates. The elements and/or compounds can be prepared by any suitable method, known in the art, for the preparation of such materials.

The term "substrate" as used herein is not meant to indicate that this component is necessarily inactive, while the other metals and/or promoters are the active species. On the contrary, the substrate can be an active part of the catalyst. The term "substrate" would merely imply that the substrate makes up a significant quantity, generally 10% or more by weight, of the entire catalyst. The promoters individually can range from 0.01% to 60% by weight of the catalyst, optionally from 0.01% to 50%, optionally from 0.01% to 40%, optionally from 0.01% to 30%, optionally from 0.01% to 20%, optionally from 0.01% to 10%, optionally from 0.01% to 5%. If more than one promoter is combined, they together generally can range from 0.01% up to 70% by weight of the catalyst, optionally from 0.01% to 50%, optionally from 0.01% to 30%, optionally from 0.01% to 15%, optionally from 0.01% to 5%. The elements of the catalyst composition can be provided from any suitable source, such as in its elemental form, as a salt, as a coordination compound, etc.

The addition of a support material to improve the catalyst physical properties is possible within the present invention. Binder material, extrusion aids or other additives can be added to the catalyst composition or the final catalyst composition can be added to a structured material that provides a support structure. For example, the final catalyst composition can include an alumina or aluminate framework as a support. Upon calcination these elements can be altered, such as through oxidation which would increase the relative content of oxygen within the final catalyst structure. The combination of the catalyst of the present invention combined with additional elements such as a binder, extrusion aid, structured material, or other additives, and their respective calcination products, are included within the scope of the invention.

In one embodiment, the catalyst can be prepared by combining a substrate with at least one promoter element. Embodiments of a substrate can be a molecular sieve, from either natural or synthetic sources. Zeolites and zeolite-like materials can be an effective substrate. Alternate molecular sieves also contemplated are zeolite-like materials such as the crystalline silicoaluminophosphates (SAPO) and the aluminophosphates (ALPO).

The present invention is not limited by the method of catalyst preparation, and all suitable methods should be considered to fall within the scope herein. Particularly effective techniques are those utilized for the preparation of solid catalysts. Conventional methods include co-precipitation from an aqueous, an organic or a combination solution-dispersion impregnation, dry mixing, wet mixing or the like, alone or in various combinations. In general, any method can be used which provides compositions of matter containing the prescribed components in effective amounts. According to an embodiment the substrate is charged with promoter via an incipient wetness impregnation. Other impregnation techniques such as by soaking, pore volume impregnation, or percolation can optionally be used. Alternate methods such as ion exchange, wash coat, precipitation, and gel formation can also be used. Various methods and procedures for catalyst preparation are listed in the technical report Manual of Methods and Procedures for Catalyst Characterization by J. Haber, J. H. Block and B. Dolmon, published in the International Union of Pure and Applied Chemistry, Volume 67, Nos 8/9, pp. 1257-1306, 1995, incorporated herein in its entirety.

The promoter elements can be added to or incorporated into the substrate in any appropriate form. In an embodiment, the promoter elements are added to the substrate by mechanical mixing, by impregnation in the form of solutions or suspensions in an appropriate liquid, or by ion exchange. In a more specific embodiment, the promoter elements are added to the substrate by impregnation in the form of solutions or suspensions in a liquid selected from the group of acetone, anhydrous (or dry) acetone, methanol, and aqueous solutions.

In another more specific embodiment, the promoter is added to the substrate by ion exchange. Ion exchange may be performed by conventional ion exchange methods in which sodium, hydrogen, or other inorganic cations that may be typically present in a substrate are at least partially replaced via a fluid solution. In an embodiment, the fluid solution can include any medium that will solubilize the cation without adversely affecting the substrate. In an embodiment, the ion exchange is performed by heating a solution containing any promoter selected from the group of Co, Mn, Ti, Zr, V, Nb, K, Cs, Ga, B, P, Rb, Ag, Na, Cu, Mg, Fe, Mo, Ce, and any combinations thereof in which the promoter(s) is(are) solubilized in the solution, which may be heated, and contacting the solution with the substrate. In another embodiment, the ion exchange includes heating a solution containing any one selected from the group of Ce, Cu, P, Cs, B, Co, Ga, and any combinations thereof. In an embodiment, the solution is heated to temperatures ranging from 50 to 120° C. In another embodiment, the solution is heated to temperatures ranging from 80 to 100° C.

The solution for use in the ion exchange method may include any fluid medium. A non-fluid ion exchange is also possible and within the scope of the present invention. In an embodiment, the solution for use in the ion exchange method includes an aqueous medium or an organic medium. In a more specific embodiment, the solution for use in the ion exchange method includes water.

The promoters may be incorporated into the substrate in any order or arrangement. In an embodiment, all of the promoters are simultaneously incorporated into the substrate. In more specific embodiment, each promoter is in an aqueous solution for ion-exchange with and/or impregnation to the substrate. In another embodiment, each promoter is in a separate aqueous solution, wherein each solution is simultaneously contacted with the substrate for ion-exchange with and/or impregnation to the substrate. In a further embodiment, each promoter is in a separate aqueous solution, wherein each solution is separately contacted with the substrate for ion-exchange with and/or impregnation to the substrate.

In an embodiment, the at least one promoter includes boron. In an embodiment, the catalyst contains greater than 0.1 wt % boron based on the total weight of the catalyst. In another embodiment, the catalyst contains from 0.1 to 3 wt % boron, optionally from 0.1 to 1 wt % boron.

The boron promoter can be added to the catalyst by contacting the substrate, impregnation, or any other method, with any known boron source. In an embodiment, the boron source is selected from the group of boric acid, boron phosphate, methoxyboroxine, methylboroxine, and trimethoxyboroxine and combinations thereof. In another embodiment, the boron source contains boroxines. In a further embodiment, the boron source is selected from the group of methoxyboroxine, methylboroxine, and trimethoxyboroxine and combinations thereof.

In an embodiment, a substrate may be previously treated with a boron source prior to an addition of at least one promoter, wherein the at least one promoter includes boron. In another embodiment, a boron treated zeolite may be combined with at least one promoter, wherein the at least one promoter includes boron. In a further embodiment, boron may be added to the catalyst system by adding at least one promoter containing boron as a co-feed with toluene and methanol. In an even further embodiment, boron may be added to the catalyst system by adding boroxines as a co-feed with toluene and methanol. The boroxines can include, methoxyboroxine, methylboroxine, and trimethoxyboroxine, and combinations thereof. The boron treated zeolite further combined with at least one promoter including boron may be used in preparing a supported catalyst such as extrudates and tablets.

When slurries, precipitates or the like are prepared, they may be dried, usually at a temperature sufficient to volatilize the water or other carrier, such as from 100° C. to 250° C., with or without vacuum. Irrespective of how the components are combined and irrespective of the source of the components, the dried composition is generally calcined in the presence of an oxygen-containing gas, usually at temperatures between about 300° C. and about 900° C. for from 1 to 24 hours. The calcination can be in an oxygen-containing atmosphere, or alternately in a reducing or inert atmosphere.

The prepared catalyst can be ground, pressed, sieved, shaped and/or otherwise processed into a form suitable for loading into a reactor. The reactor can be any type known in the art such as a fixed bed, fluidized bed, or swing bed reactor. Optionally an inert material can be used to support the catalyst bed and to place the catalyst within the bed. Depending on the catalyst, a pretreatment of the catalyst may, or may not, be necessary. For the pretreatment, the reactor can be heated to elevated temperatures, such as 200° C. to 900° C. with an air flow, such as 100 mL/min, and held at these conditions for a length of time, such as 1 to 3 hours. Then, the reactor can be brought to the operating temperature of the reactor, for example 300° C. to 550° C., or optionally down to any desired temperature, for instance down to ambient temperature to remain under a purge until it is ready to be put in service. The reactor can be kept under an inert purge, such as under a nitrogen or helium purge.

Embodiments of reactors that can be used with the present invention can include, by non-limiting examples: fixed bed reactors; fluid bed reactors; moving bed reactors; and entrained bed reactors. Reactors capable of the elevated temperature and pressure as described herein, and capable of enabling contact of the reactants with the catalyst, can be considered within the scope of the present invention. Embodiments of the particular reactor system may be determined based on the particular design conditions and throughput, as by one of ordinary skill in the art, and are not meant to be limiting on the scope of the present invention. An example of a suitable reactor can be a fluid bed reactor having catalyst regeneration capabilities. This type of reactor system employing a riser can be modified as needed, for example by insulating or heating the riser if thermal input is needed, or by jacketing the riser with cooling water if thermal dissipation is required. These designs can also be used to replace catalyst while the process is in operation, by withdrawing catalyst from the regeneration vessel from an exit line or adding new catalyst into the system while in operation.

In another embodiment, the one or more reactors may include one or more catalyst beds. In the event of multiple beds, an inert material layer can separate each bed. The inert material can comprise any type of inert substance. In an embodiment, a reactor includes between 1 and 25 catalyst beds. In a further embodiment, a reactor includes between 2 and 10 catalyst beds. In a further embodiment, a reactor includes between 2 and 5 catalyst beds. In addition, the co-feed, the $C_1$ source and/or toluene may be injected into a catalyst bed, an inert material layer, or both. In a further embodiment, the toluene feed is injected prior to the first catalyst bed while at least a portion of the $C_1$ source and/or at least a portion of the co-feed are injected into one or more catalyst bed(s) along the reactor to control the toluene: $C_1$ source in each catalyst bed.

In an alternate embodiment, the entire $C_1$ source is injected into a catalyst bed(s), all of the toluene feed is injected into an inert material layer(s) and all of the co-feed is injected into one of: the catalyst bed(s), the inert material layer(s), or any combination thereof. In another embodiment, at least a portion of the toluene feed is injected into a catalyst bed(s), at least a portion of the co-feed is injected into a catalyst bed(s), and at least a portion the $C_1$ source is injected into an inert material layer(s). In a further embodiment, all of the toluene feed and all of the co-feed are injected into a catalyst bed(s) and the entire $C_1$ source is injected into an inert material layer(s).

The toluene and $C_1$ source coupling reaction may have a toluene conversion percent greater than 0.01 mol %. In an embodiment the toluene and $C_1$ source coupling reaction is capable of having a toluene conversion percent in the range of from 0.05 mol % to 40 mol %. In a further embodiment the toluene and $C_1$ source coupling reaction is capable of having a toluene conversion in the range of from 2 mol % to 40 mol %, optionally from 5 mol % to 35 mol %, optionally from 10 mol % to 30 mol %.

In an embodiment the toluene and $C_1$ source coupling reaction is capable of selectivity to styrene greater than 1 mol %. In another embodiment, the toluene and $C_1$ source coupling reaction is capable of selectivity to styrene in the range of from 1 mol % to 99 mol %. In an embodiment the toluene to a $C_1$ source coupling reaction is capable of selectivity to ethylbenzene greater than 1 mol %. In another embodiment, the toluene and $C_1$ source coupling reaction is capable of selectivity to ethylbenzene and styrene in the range of from 1 mol % to 99 mol %. In an embodiment the toluene and $C_1$ source coupling reaction is capable of yielding less than 0.5 mol % of undesirable ring alkylated products such as xylenes.

EXAMPLES

The alkylation of toluene with a carbon source over a catalyst, such as a basic zeolite catalyst, may yield ethylbenzene and styrene as major products as well as other by-products and unreacted reactants. It is desirable to optimize styrene selectivity in order to improve the economics of styrene production. The following examples demonstrate that styrene selectivity can be improved by adding a co-feed, such as carbon monoxide, hydrogen, or water, along with the reactant feed to the reactor.

Comparative Example

The examples herein used a X-type zeolite promoted with cesium and boron, labeled as (Cs, B)/X. The procedure used to produce the cesium ion-exchanged zeolite material used a glass cylinder (2" inside diameter), fitted with a sintered glass disk and stopcock at the lower end, that was charged with 544-HP zeolite (100 g, W.R. Grace) and CsOH (400 mL, 1.0 M in water). The mixture was then brought to 90° C. and allowed to stand for 4 hours. The liquid was drained from the zeolite material and another aliquot of CsOH (400 mL of 1.0 M solution in water) was added and allowed to stand for 3 hours at 90° C. The liquid was drained from the zeolite material and another aliquot of CsOH (400 mL of 1.0 M solution in water) was added and allowed to stand for 15 hours at 90° C. The liquid was drained from the zeolite material and dried at 150° C. for 1.5 hours.

A deposition of 1.4 wt % boron (by weight of final zeolite material) onto the cesium ion-exchanged zeolite material was then performed. The cesium ion-exchanged zeolite material (35 g) was treated with a solution of boric acid (2.8 g) dissolved in acetone (500 mL) at room temperature for 2 hours. The (Cs, B)/X material was then dried at 110° C. for 20 hours.

Stainless steel reactor details: A stainless steel tube with 0.5-inch outer diameter and 0.465 inch internal diameter was filled with crushed quartz of 850-2000 µm size (to a height of about 10 inches, 29.2 mL), then the catalyst (to a height of 3.0 inches; 6.6 mL, 3.35 g) at sizes ranging from 250-425 µm, and then more crushed quartz of 850-2000 µm size (to a height of about 17 inches, 37.2 mL) such that a 0.125 inch stainless steel thermowell was positioned in the middle of the catalyst bed. The reactor was installed in a 3-zone furnace and heated to 500° C. and held for 2 hours while passing nitrogen through it at 150 cc/min. The reactor was then cooled to the reaction temperature of 420° C.

The feed consisted of toluene and methanol in a 4:1 molar ratio to conduct a "normal" alkylation reaction. Reaction conditions used were a temperature of 420° C. and a pressure of 15 psig. The flow rates were corrected for temperature. The effluent was monitored by an on-line gas chromatograph. The results are shown in Table 1.

TABLE 1

| Catalyst | Contact Time (sec) | Time On Stream (hh:mm) | $X_{Tol}$ | $S_{Bz}$ | $S_{Xyl}$ | $S_{EB}$ | $S_{Sty}$ | $X_{MeOH}$ |
|---|---|---|---|---|---|---|---|---|
| Cs, B/X | 2.6 | 1:50 | 3.5 | 1.2 | 0.5 | 80.9 | 16.4 | 60.5 |
| Cs, B/X | 2.6 | 2:35 | 3.6 | 1.1 | 0.4 | 80.9 | 16.9 | 57.0 |
| Cs, B/X | 2.6 | 4:45 | 2.0 | 1.8 | 0.5 | 83.7 | 13.7 | 37.6 |
| Cs, B/X | 2.6 | 5:50 | 2.0 | 1.8 | 0.5 | 84.5 | 12.9 | 60.0 |

Example 1

The influence of water on improving catalyst lifetime and functionality was examined. This example involved adding water to the catalyst bed to simulate the amount of water present during 4 mol % conversion of toluene. In the alkylation of toluene with a $C_1$ source, one mole of water is a co-product with each mole of styrene produced. Thus, if water caused the destruction of active sites we would observe a low toluene conversion upon adding the toluene and methanol. The catalyst was a X-type zeolite promoted with cesium and boron, labeled as (Cs, B)/X and is the same catalyst as used in the comparative example above. The same reactor was used with a temperature of 420° C. and pressure of 15 psig The catalyst was subjected to the flow of water at a rate of 0.004 mL/min with nitrogen at a rate of 115 mL/min to simulate 4% toluene conversion coming from a preceding bed at a 2.5 second contact time for 4 hours. Then the feed was switched to toluene and methanol in a 4:1 molar ratio to conduct a "normal" alkylation reaction. Reaction conditions used were a temperature of 420° C. and pressure of 15 psig. As shown in Table 2, toluene conversion, selectivity to benzene and selectivity to xylene were essentially uninfluenced by the pretreatment with water. The selectivity to EB decreased substantially as compared to the comparative example without pretreatment. The selectivity to styrene increased substantially as compared to the comparative example without pretreatment. The selectivity to EB and styrene remained consistent with time on stream.

TABLE 2

The Effect of Water Added to the Catalyst Bed of an ATM Process.

| Catalyst | Contact Time (sec) | Time On Stream (hh:mm) | $X_{Tol}$ | $S_{Bz}$ | $S_{Xyl}$ | $S_{EB}$ | $S_{Sty}$ | $X_{MeOH}$ |
|---|---|---|---|---|---|---|---|---|
| Cs, B/X | 2.6 | 2:00 | 3.6 | 1.5 | 0.4 | 23.5 | 55.3 | 100 |
| Cs, B/X | 2.6 | 2:45 | 4.2 | 1.1 | 0.3 | 22.8 | 57.6 | 100 |
| Cs, B/X | 2.6 | 3:50 | 3.9 | 1.1 | 0.3 | 23.4 | 56.1 | 100 |
| Cs, B/X 4 hr steaming 0.004 mL/min $H_2O$ and 115 mL/min $N_2$ prior to ATM reaction | 2.6 | 4:15 | 3.7 | 1.1 | 0.3 | 24.2 | 55.3 | 100 |

Example 2

The next example was carried out with toluene, methanol, and water as a combined feed stream to determine if water was competing with the active sites of the catalyst. This experiment had conditions equivalent to Example 1, except the water was added with the toluene and methanol feed in an amount of 0.00022 moles of water for every 1 mole of methanol. Reaction conditions used were a temperature of 420° C., pressure of 15 psig and a molar ratio of toluene to methanol of 4:1. Again, as shown in Table 3, the toluene conversion was essentially uninfluenced by the presence of water as compared to the comparative example. Over the 4-5 hours of use, the catalyst did not deactivate as quickly as when water was absent. The selectivity to EB increased with time on stream while the selectivity to styrene decreased with time on stream. Toluene conversion, selectivity to benzene and selectivity to xylene were essentially uninfluenced by the addition of water in the feed. The selectivity to EB decreased substantially while the selectivity to styrene increased substantially as compared to the comparative example without the addition of water in the feed.

TABLE 3

The Effect of Water Added as a co-Feed with Toluene and $C_1$ source in an ATM process.

| Catalyst | Contact Time (sec) | Time On Stream (hh:mm) | $X_{Tol}$ | $S_{Bz}$ | $S_{Xyl}$ | $S_{EB}$ | $S_{Sty}$ | $X_{MeOH}$ |
|---|---|---|---|---|---|---|---|---|
| Cs, B/X | 2.6 | 2:29 | 3.4 | 1.4 | 0.3 | 33 | 66 | 100.0 |
| Cs, B/X | 2.6 | 3:01 | 3.3 | 1.5 | 0.3 | 36 | 62 | 100.0 |
| Cs, B/X | 2.6 | 4:15 | 3.2 | 1.4 | 0.3 | 38 | 61 | 100.0 |
| Cs, B/X 0.004 mL/min $H_2O$ co-feed | 2.6 | 4:55 | 2.8 | 1.7 | 0.3 | 39 | 59 | 100.0 |

Example 3

In this example, the influence of hydrogen as a co-feed with toluene and methanol was investigated. An experiment was conducted on the (Cs, B)/X catalyst of the comparative example using 33 mL/min hydrogen as a co-feed to further investigate potential active site poisons. Reaction conditions used were a temperature of 420° C. pressure of 15 psig and a molar ratio of toluene to methanol of 4:1. Hydrogen as a co-feed was added in an amount of 0.115 moles of hydrogen for every mole of methanol.

TABLE 4

The Effect of Hydrogen Added as a co-Feed with Toluene and $C_1$ source in an ATM process.

| Catalyst | Contact Time (sec) | Time On Stream (hh:mm) | $X_{Tol}$ | $S_{Bz}$ | $S_{Xyl}$ | $S_{EB}$ | $S_{Sty}$ | $X_{MeOH}$ |
|---|---|---|---|---|---|---|---|---|
| Cs, B/X | 2.5 | 2:45 | 2.3 | 1.5 | 0.5 | 43 | 55 | 87.4 |
| Cs, B/X | 2.5 | 3:46 | 2.2 | 1.4 | 0.6 | 45 | 53 | 100.0 |
| Cs, B/X | 2.5 | 5:57 | 1.9 | 1.5 | 0.7 | 48 | 50 | 93.0 |
| 33 mL/min $H_2$ co-feed | | 6:54 | 1.7 | 1.6 | 0.7 | 50 | 48 | 91.7 |

According to the results in Table 4, the addition of hydrogen increased selectivity to EB with time on stream while the selectivity to styrene decreased with time on stream. Toluene conversion, selectivity to benzene and selectivity to xylene were essentially uninfluenced by the addition of hydrogen in the feed. The selectivity to EB decreased substantially as compared to the comparative example. The selectivity to styrene increased substantially as compared to the comparative example without the addition of hydrogen in the feed.

Example 4

In this example, the influence of CO as a co-feed with toluene and a $C_1$ source was investigated. An ATM experiment was conducted on the (Cs, B)/X catalyst as used in the other examples herein, using 23 mL/min CO as a co-feed to further investigate potential active site poisons. Normal reaction conditions were used of a molar ratio of toluene to methanol of 4:1, temperature of 420° C., and pressure of 15 psig. Carbon monoxide as a co-feed was added in an amount of 0.001 moles of CO for every 4 moles of toluene and for every 1 mole of methanol.

TABLE 5

The Effect of CO Added as a co-Feed with Toluene and $C_1$ source in an ATM process.

| Catalyst | Contact Time (sec) | Time On Stream (hh:mm) | $X_{Tol}$ | $S_{Bz}$ | $S_{Xyl}$ | $S_{EB}$ | $S_{Sty}$ | $X_{MeOH}$ |
|---|---|---|---|---|---|---|---|---|
| Cs, B/X | 2.7 | 2:39 | 3.5 | 1.7 | 0.3 | 34 | 64 | 100.0 |
| Cs, B/X | 2.7 | 3:30 | 3.1 | 1.8 | 0.4 | 36 | 62 | 100.0 |
| Cs, B/X | 2.7 | 4:38 | 2.8 | 1.9 | 0.4 | 38 | 60 | 100.0 |
| 23 mL/min CO co-feed | | 5:15 | 2.6 | 1.9 | 0.4 | 40 | 58 | 100.0 |

The results in Table 5 show that an improvement in styrene selectivity was obtained with CO as a co-feed. Toluene conversion, selectivity to benzene and selectivity to xylene were essentially uninfluenced by the addition of CO in the feed. The selectivity to EB decreased substantially as compared to the comparative example. The selectivity to styrene increased substantially as compared to the comparative example without the addition of CO in the feed. Furthermore, the use of CO as co-feed did not require the additional energy consumption necessary to convert water to steam.

The term "conversion" refers to the percentage of reactant (e.g. toluene) that undergoes a chemical reaction.

$X_{Tol}$=conversion of toluene (mol %)=$(Tol_{in}-Tol_{out})/Tol_{in}\times 100$ $X_{meoH}$=conversion of methanol to styrene+ethylbenzene (mol %)=$(MeOH_{in}-MeOH_{out})/MeOH_{in}\times 100$ The term "molecular sieve" refers to a material having a fixed, open-network structure, usually crystalline, that may be used to separate hydrocarbons or other mixtures by selective occlusion of one or more of the constituents, or may be used as a catalyst in a catalytic conversion process.

Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

The term "regenerated catalyst" refers to a catalyst that has regained enough activity to be efficient in a specified process. Such efficiency is determined by individual process parameters.

The term "selectivity" refers to the relative activity of a catalyst in reference to a particular compound in a mixture. Selectivity is quantified as the proportion of a particular product relative to all other products.

$S_{Sty}$=selectivity of toluene to styrene (mol %)=$Sty_{out}/Tol_{converted}\times 100$ $S_{Bz}$=selectivity of toluene to benzene (mol %)=$Benzene_{out}/Tol_{converted}\times 100$ $S_{EB}$=selectivity of toluene to ethylbenzene (mol %)=$EB_{out}/Tol_{converted}\times 100$ $S_{Xyl}$=selectivity of toluene to xylenes (mol %)=$Xylenes_{out}/Tol_{converted}\times 100$ $S_{Sty+EB}$(MEOH)=selectivity of methanol to styrene+ethylbenzene (mol %)=$(Sty_{out}+EB_{out})/MeOH_{converted}\times 100$ The term "spent catalyst" refers to a catalyst that has lost enough catalyst activity to no longer be efficient in a specified process. Such efficiency is determined by individual process parameters.

The term "zeolite" refers to a molecular sieve containing an aluminosilicate lattice, usually in association with some aluminum, boron, gallium, iron, and/or titanium, for example. In the following discussion and throughout this disclosure, the terms molecular sieve and zeolite will be used more or less interchangeably. One skilled in the art will recognize that the teachings relating to zeolites are also applicable to the more general class of materials called molecular sieves.

The various embodiments of the present invention can be joined in combination with other embodiments of the invention and the listed embodiments herein are not meant to limit the invention. All combinations of various embodiments of the invention are enabled, even if not given in a particular example herein.

While illustrative embodiments have been depicted and described, modifications thereof can be made by one skilled in the art without departing from the spirit and scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.).

Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. Also, it is within the scope of this disclosure that the embodiments disclosed herein are usable and combinable with every other embodiment disclosed herein, and consequently, this disclosure is enabling for any and all combinations of the embodiments disclosed herein. Other and further embodiments, versions and examples of the invention may be devised without departing from the basic scope thereof and the scope thereof is determined by the claims that follow.

What is claimed is:

1. A process for making styrene comprising:
providing toluene, a co-feed, and a C1 source to a reactor comprising a catalyst comprising X zeolite and at least one promoter selected from the group consisting of Ce, Cu, P, Cs, B, Co, Ga, and combinations thereof, wherein the C1 source is selected from the group consisting of methanol, formaldehyde formalin, trioxane, methylformcel, paraformaldehyde, methylal, dimethyl ether, and combinations thereof; and
reacting toluene with the C1 source in the presence of the catalyst and the co-feed to form a product stream comprising ethylbenzene and styrene;
wherein the co-feed is selected from the group consisting of carbon monoxide, hydrogen, and combinations thereof.

2. The process of claim 1, wherein the catalyst comprises B and Cs supported on the X zeolite.

3. The process of claim 1, wherein the co-feed is simultaneously fed to the reactor with the toluene and the $C_1$ source.

4. The process of claim 1, wherein the co-feed is present in amounts of 0.0001 to 15 wt % of the combined feed of the toluene, co-feed and $C_1$ source.

5. The process of claim 1, resulting in a toluene conversion from 2 to 50%.

6. The process of claim 1, having a selectivity to styrene from 15 to 80%.

7. The process of claim 1, having a selectivity to ethylbenzene from 15 to 80%.

8. A method of making styrene, comprising:
providing a reactor comprising a catalyst comprising X zeolite and at least one promoter selected from the group consisting of Ce, Cu, P, Cs, B, Co, Ga, and combinations thereof;
providing a reactant feed stream comprising toluene and a C1 source selected from the group consisting of methanol, formaldehyde, formalin, trioxane, methylformcel, paraformaldehyde, methylal, dimethyl ether, and combinations thereof;
providing a co-feed selected from the group consisting of carbon monoxide, hydrogen, and combinations thereof; and
reacting the toluene with the C1 source in the presence of the co-feed and the catalyst to form a product stream comprising ethylbenzene and styrene.

9. The method of claim 8, resulting in a toluene conversion of from 2 to 50%.

10. The method of claim 8, having a selectivity to styrene from 15 to 80%.

11. The method of claim 8, having a selectivity to ethylbenzene from 15 to 80%.

12. A method of producing styrene comprising:
providing toluene, a co-feed, and a C1 source to a reactor comprising a catalyst;
reacting toluene with the C1 source in the presence of the catalyst and the co-feed to form a product stream comprising ethylbenzene and styrene;
wherein the C1 source is selected from the group consisting of methanol, formaldehyde, formalin, trioxane, methylformcel, paraformaldehyde, methylal, dimethyl ether, and combinations thereof;
wherein the catalyst comprises boron and cesium supported on an X-type zeolite;
wherein the co-feed is selected from the group consisting carbon monoxide, hydrogen, and combinations thereof
wherein the reaction gives a toluene conversion of from 2 to 50%, a selectivity to styrene from 15 to 80%, and a selectivity to ethylbenzene from 15 to 80%.

* * * * *